US007018648B2

(12) United States Patent
Sournac et al.

(10) Patent No.: US 7,018,648 B2
(45) Date of Patent: Mar. 28, 2006

(54) TRANSDERMAL DEVICE FOR ADMINISTERING TESTOSTERONE OR ONE OF THE DERIVATIVES THEREOF

(75) Inventors: Michel Sournac, Toulouse (FR); Laurent Liorzou, L'Union (FR); Joël Bougaret, Lanta (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 0 days.

(21) Appl. No.: 09/979,757

(22) PCT Filed: May 18, 2000

(86) PCT No.: PCT/FR00/01345

§ 371 (c)(1),
(2), (4) Date: Nov. 26, 2001

(87) PCT Pub. No.: WO00/71133

PCT Pub. Date: Nov. 30, 2000

(65) Prior Publication Data

US 2005/0100586 A1    May 12, 2005

(30) Foreign Application Priority Data

May 19, 1999  (FR) .................................. 99 06367

(51) Int. Cl.
 *A61K 13/00* (2006.01)
 *A61K 9/14* (2006.01)
 *A61L 15/16* (2006.01)
 *A61F 13/02* (2006.01)
(52) U.S. Cl. ............... 424/449; 424/400; 424/447; 424/448; 424/484; 424/487
(58) Field of Classification Search ............... 424/400, 424/443, 448, 449, 484, 485, 486, 487, 488; 514/946, 964
See application file for complete search history.

(56) References Cited

U.S. PATENT DOCUMENTS 4,357,934 A * 11/1982 Fahim ...................... 600/33

(Continued)

FOREIGN PATENT DOCUMENTS

JP     407328053 A  * 12/1995
WO    WO98/37871   *  9/1998

OTHER PUBLICATIONS

Myers et al, Quetiapine-induced diabetes with metabolic acidosis, Int Clin Psychopharmacology, May 2004; 19(3): 169-71.*
Coppola, Endocrine diseases and male infertility, Minerva Med, Sep. 1997; 88(9): 355-63.*

*Primary Examiner*—Gary L. Kunz
*Assistant Examiner*—S. Gollamudi
(74) *Attorney, Agent, or Firm*—Hueschen and Sage (57) ABSTRACT

The invention relates to a self-adhesive transdermal device for the administration of testosterone and/or at least one of the derivatives thereof, comprising successively at least one support layer, a self-adhesive matrix layer and a detachable protective layer, whereby the matrix layer comprises at least one self-adhesive polymer, at least one formulating adjuvant for the matrix layer, at least one solvent chosen from the group made up of solvents of testosterone or the derivatives thereof and testosterone and/or at least one of the derivatives thereof in an oversaturated solution. The device has excellent testosterone permeation qualities and excellent cutaneous tolerance and adhesion qualities. The invention also relates to a method for the production of said device and the use thereof for a medicament, i.e. within the framework of a testosterone replacement therapy.

26 Claims, 8 Drawing Sheets

U.S. PATENT DOCUMENTS 5,079,008 A * 1/1992 Sinnreich et al. ............ 424/448
5,152,997 A * 10/1992 Ebert et al. .................. 424/449
5,492,911 A * 2/1996 Stief ........................ 514/234.2
5,676,968 A * 10/1997 Lipp et al. ................... 424/448
5,693,335 A * 12/1997 Xia et al. ..................... 424/448
5,906,830 A * 5/1999 Farinas et al. ............... 424/448
6,113,940 A * 9/2000 Brooke et al. ............... 424/449
6,335,031 B1 * 1/2002 Asmussen et al. ........... 424/449

* cited by examiner

FIG. 3a : Cumulative amounts

FIG. 3b : Flow

FIG. 4a : Cumulative amounts

FIG. 4b : Flow

FIG. 4c : Cumulative amounts

FIG. 4d : Flow

TRANSDERMAL DEVICE FOR ADMINISTERING TESTOSTERONE OR ONE OF THE DERIVATIVES THEREOF

The present invention relates to a self-adhesive transdermal device for administering testosterone and/or at least one derivative thereof, to a process for preparing this device and to the use of this device for a medicinal product, especially in the context of a testosterone replacement therapy.

Transdermal devices are pharmaceutical forms which allow the percutaneous administration of certain active principles, more particularly in the context of chronic pathologies, or even as a preventive measure. Those intended for hormone replacement therapy in women have more particularly been studied in recent years, in the form of estradiol-based transdermal devices, or even devices combining estradiol with a compound with progestative action.

Along the same lines, certain devices for promoting the administration of male hormones, and essentially testosterone-based hormones, have recently appeared.

Testosterone, known under the systematic nomenclature as 17-hydroxyandrost-4-en-3-one, is the main circulating hormone of an androgenic type; under the action of 5-α-reductase, it is converted into dihydrotestosterone, the hormone responsible for sexual differentiation. Testosterone has been available for many years in the form of injectable preparations and capsules, indicated in the therapeutic treatment of male hypogonadism. These forms have many drawbacks associated either with problems of absorption (or permeation through the skin) or with poor adherence of the patient to the injection treatment. Thus, the first testosterone-based transdermal forms appeared.

Among transdermal devices, reservoir devices are generally distinguished from matrix devices. In reservoir devices, the active ingredient is contained in a gel, usually an aqueous-alcoholic gel, arranged between a support film and a control membrane. In the case of devices adhering over their entire surface, a layer of a material that is permeable to the active ingredient and adhesive—or intermediate permeation membrane—is present between the surface of the skin and the release-controlling membrane. In the other cases, this layer is at the periphery. In matrix devices, the active ingredient is contained in one or more matrix layers (generally based on self-adhesive polymers). In this case, a direct contact with the skin does not at the very least necessitate the presence of an intermediate permeation membrane.

One of the major problems concerning the transdermal administration of various active principles is the slow penetration or, in other words, the slow speed of permeation of the active principle through the skin.

This problem of permeation of the active principle through the skin is all the more crucial in the case of a testosterone replacement therapy in order to obtain the desired physiological levels, most particularly in men, in which the physiological levels to be reached are naturally higher than those in women.

Thus, it is known that the transdermal administration of testosterone in therapeutic amount in men requires either the presence of several permeation promoters in the transdermal device, or the design of a device which can only be used on the skin of the scrotum, that is to say the region of the male body where the skin is thinnest, which penalizes the adherence of the patient to the treatment.

Various publications in particular mention transdermal devices whose reservoir or matrix comprises testosterone permeation promoters.

For example, U.S. Pat. No. 5,152,997 describes a transdermal device of reservoir type, involving a combination of several promoters, such as ethanol, methyl laurate and glyceryl monooleate. This device allows the release of about 13 μg/cm$^2$/hr of testosterone from a patch applied to standard regions for the application of a trans-dermal device, for instance the arm, the abdomen or the back.

However, as is the case for this device of U.S. Pat. No. 5,152,997, a transdermal device comprising permeation promoters is usually of entirely unsatisfactory skin tolerance, which may be explained by an undesirable interaction of the permeation promoters with the skin.

Moreover, it is also known that the formulation of a transdermal device with a self-adhesive polymer matrix presents the problem of the stability of the testosterone in the matrix, in particular when it is desired to have a state of supersaturation of the testosterone in the matrix for a greater release of testosterone, most particularly in the context of a testosterone replacement therapy in men.

Finally, one of the specific problems of transdermal devices with a self-adhesive polymer matrix is the degree of adhesion, which must be sufficient to allow good release of the active principle, by occlusive contact with the skin.

It has now been found, entirely surprisingly and unexpectedly, that the choice of certain components makes it possible to obtain a self-adhesive transdermal device which has not only excellent properties of testosterone permeation, but also of skin tolerance and adhesion, with a view to use for a testosterone replacement therapy, especially in men.

One subject of the present invention is thus a self-adhesive transdermal device for administering testosterone and/or at least one derivative thereof, characterized in that it comprises, successively, at least, one support layer, one self-adhesive matrix layer and one detachable protective layer, said matrix layer comprising, relative to the total weight of the said matrix layer:

a) 40% to 80% by weight of at least one self-adhesive polymer selected from polymers of acrylic type, with an acid number of between 10 and 70, with an acid functionality and a glass transition temperature of between −70° C. and −20° C.;

b) 5% to 25% by weight of at least one formulation adjuvant for the matrix layer selected from polymers with a number-average molecular mass of between 2500 and 3000000;

c) 5% to 20% by weight of at least one solvent selected from the group consisting of solvents for testosterone and derivatives thereof, in which the solubility of the testosterone or derivative thereof is between 5% and 20% m/m;

d) 2% to 10% by weight of testosterone and/or at least one derivative thereof, as a supersaturated solution.

In particular, the acid functionality of the self-adhesive polymer is such that it has an acid number of between 10 and 70 and in particular between 30 and 50.

Preferably, an acrylic copolymer of low to medium molecular mass, that is to say a number-average molecular mass of between 200 000 and 400 000 as measured by the technique of gel permeation chromatography (GPC), will be used as self-adhesive polymer.

The acid functionality results from the presence of acrylic acid among the base monomers, giving it an acid number as measured by the standard techniques well known to those skilled in the art (especially the neutralization technique).

It should thus be understood that the self-adhesive polymer used for the matrix layer of the device according to the invention characteristically contains free carboxylic acid side groups.

Preferably, the self-adhesive polymer is a polymer of (meth)acrylic acid monomer and of at least one monomer chosen from the group consisting of C1–C6 alkyl (meth)acrylate, 2-(C1–C6 alkyl)hexyl (meth)acrylate, vinyl acetate, glycidyl (meth)acrylate and 2-hydroxy(C1–C6 alkyl) (meth)acrylate monomers.

More particularly, the self-adhesive polymer is a polymer of (meth)acrylic acid monomer and of at least one monomer chosen from the group consisting of methyl (meth)acrylate, butyl (meth)acrylate, 2-ethylhexyl (meth)acrylate, vinyl acetate, glycidyl (meth)acrylate and 2-hydroxyethyl (meth) acrylate monomers.

The self-adhesive polymer preferably has a vinyl acetate content of between 1 and 10% by weight relative to the total weight of the base monomers. Such an acrylic copolymer is, for example, Duro-Tak® 387-2052 or 87-2052 from the company National Starch & Chemical, which is a self-crosslinked adhesive available in the form of an organic solution with a theoretical density close to 0.92 g/cm$^3$ and a Brookfield viscosity (at 25° C., 12 rpm, spindle No. 3) in the region of 2 800 mPa.s.

According to one preferred embodiment, the matrix layer of the device according to the invention is crosslinked. In particular, the self-adhesive polymer is preferably crosslinked to the extent that cohesion of the resulting matrix and thus of the device comprising it is thereby reinforced. One method for obtaining a crosslinked self-adhesive polymer for the device according to the invention is described in particular in the examples below.

Mention will be made in particular of aluminum salts such as aluminum acetylacetonate, but any other crosslinking agent known to those skilled in the art may be used.

Needless to say, the matrix layer of the device according to the invention may in particular be noncrosslinked, that is to say in particular that it is possible for the self-adhesive polymer not to be crosslinked, as illustrated in example 6 below.

Among the formulation adjuvants which may be present in the matrix layer of the device according to the invention, chosen from polymers with a number-average molecular mass of between 2 500 and 3 000 000, mention may be made of cellulose derivatives and more particularly sodium carboxymethylcellulose with a molecular mass of between 90 000 and 700 000, derivatives of alkylcellulose type, for instance hydroxyethylcellulose or hydroxypropylcellulose, high molecular weight polysaccharides and more particularly xanthan gums, and polymers of the 1-vinyl-2-pyrrolidone type with a molecular mass of between 2 500 and 3 000 000.

In particular, the formulation adjuvant is preferably chosen from the group consisting of polymers of 1-vinyl-2-pyrrolidone monomer, polysaccharides and cellulose derivatives, and mixtures thereof.

More specifically, the formulation adjuvant is preferably chosen from the group consisting of polyvinylpyrrolidone, xanthan gums and sodium carboxymethylcellulose, and mixtures thereof.

Preferably, polyvinylpyrrolidone, whose better solubility in alcoholic medium facilitates the dispersion in an adhesive matrix of the device according to the invention, taking into account the process described below for preparing the device according to the invention, will be used most particularly.

The solvent present in the matrix layer of the device according to the invention is a solvent for testosterone and/or derivatives thereof, preferably chosen from the group consisting of N,N-diethyl-m-toluamide, 2-octyldodecanol, crotamiton, propylene glycol dipelargonate and mixtures thereof. N,N-diethyl-m-toluamide is most particularly preferred.

According to one preferred embodiment, the matrix layer of the device according to the invention is such that the self-adhesive polymer is a polymer of acrylic acid, 2-ethylhexyl acrylate, vinyl acetate and butyl acrylate monomers, this polymer being crosslinked and having an acid number between 10 and 70 and also a glass transition temperature of between −100° C. and −10° C., the formulation adjuvant is polyvinylpyrrolidone with a number-average molecular mass of between 44 000 and 54 000, and the solvent is N,N-diethyl-m-toluamide.

The testosterone is present in unmodified form (17β-hydroxyandrost-4-en-3-one) in the matrix layer of the device according to the invention, or in the form of a derivative thereof.

According to the invention, the expression "testosterone derivatives" means not only its esters such as, for example, the acetate, enanthate, propionate, isobutyrate, undecanoate and cypionate forms, but also derivatives such as those containing a substituent at least in position 6α or 7α. Preferably, mention may be made of 7α-methyltestosterone, 7α-methyl-19-nortestosterone, 7α-methyl-11β-hydroxytestosterone, 7α,17-dimethyltestosterone, 7α,17-dimethyl-11β-hydroxytestosterone, 7α,17-dimethyl-19-nortestosterone, 7α,17-dimethyl-11β-hydroxy-19-nortestosterone, 6α-methyltestosterone, 6α-methyl-19-nortestosterone, 6α-methyl-11β-hydroxytestosterone, 6α,17-dimethyltestosterone, 6α,17-dimethyl-11β-hydroxytestosterone, 6α,17-dimethyl-19-nortestosterone and 6α,17-diemthyl-11β-hydroxy-19-nortestosterone.

According to one particularly preferred embodiment, the matrix layer of the device according to the invention comprises, relative to its total weight:

a) 63% to 73% by weight of at least one self-adhesive polymer of acrylic acid, 2-ethylhexyl acrylate, vinyl acetate and butyl acrylate monomers, this polymer being crosslinked and having an acid number of between 10 and 70 and also a glass transition temperature of between −100° C. and −10° C.;

b) 5% to 25% by weight of polyvinylpyrrolidone with a number-average molecular mass of between 44 000 and 54 000;

c) 9% to 15% by weight of N,N-diethyl-m-toluamide;

d) 4% to 6% by weight of testosterone.

The matrix layer of the device according to the invention as described above may advantageously also comprise at least one antioxidant chosen from the group consisting of butylhydroxytoluene (BHT), butylhydroxyanisole (BHA), ascorbyl palmitate, α-tocopherol and its esters, citric acid and propyl gallate, and mixtures thereof.

Preferably, the antioxidant is present in the matrix layer, relative to the total weight of said matrix layer, in a proportion of between 0.1% and 2% by weight.

The support layer for the device according to the invention must be such as those generally used in the formulation of transdermal devices, that is to say occlusive and inert with respect to the constituents of the matrix layer. Among the products generally used, mention should be made of polyethylene, polypropylene and polyester films, multilayer complexes consisting of the above materials combined, for example, with thin layers of aluminum, and combinations of copolymers of vinyl acetate and of ethylene in the form of films or foam. Preferably, either a polyester support film, this film being used either directly or via a transfer principle, or a multilayer complex or low-density polyethylene type and polyvinylidene chloride, the latter then being used by transfer, will preferably be used.

Before its use, the device obviously comprises, on the matrix layer side, which is intended to be in contact with the patient's skin, a detachable protective layer which protects the adhesive matrix. This detachable protective layer must in particular be made of a material with good cutting properties and which is inert with respect to the components of the matrix; among the products most often used, mention should be made of paper, polyester and polyvinyl chloride films. Preferably, a polyester film that has been cut to shape beforehand will be used so as to facilitate its removal before use by the patient.

The transdermal device according to the invention will be contained before use in a leaktight protection of sachet type with the aid of polyethylene-aluminum complex films, or of blister type.

The matrix device according to the invention has many advantages, which may be described as follows.

Compared with the existing pharmaceutical forms, and more particularly compared with the transdermal forms already marketed, the device according to the invention is distinguished surprisingly by an excellent compromise between adhesion and skin tolerance.

Figure 1:
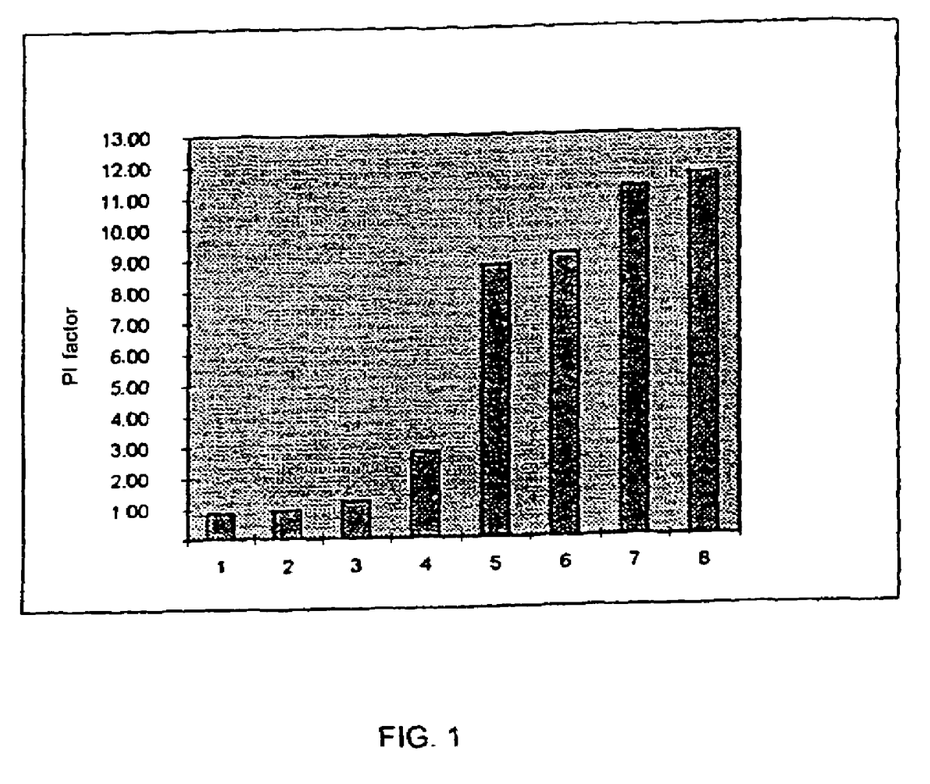
FIG. 1 represents the permeation indices (PIs), also known as the "enhancement factors" for comparing in vitro the promoting effect of different products.
Figure 2:
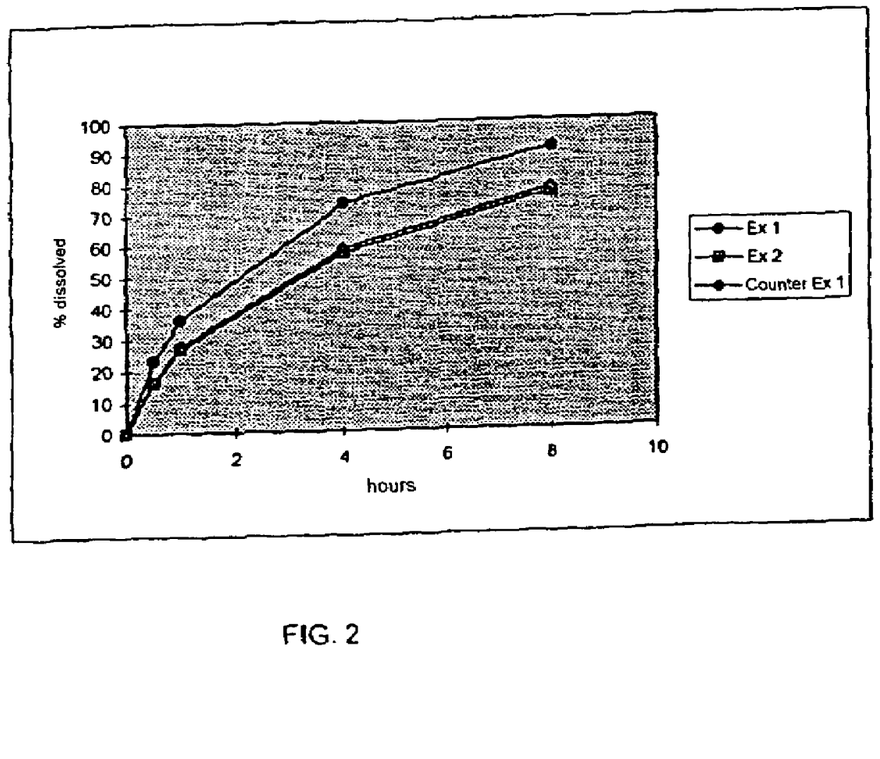
FIG. 2 represents the amounts of testosterone released in vitro as a function of time in the case of the various formulations of examples 1 and 2 according to the invention and of the counterexample 1.
Figure 3A:
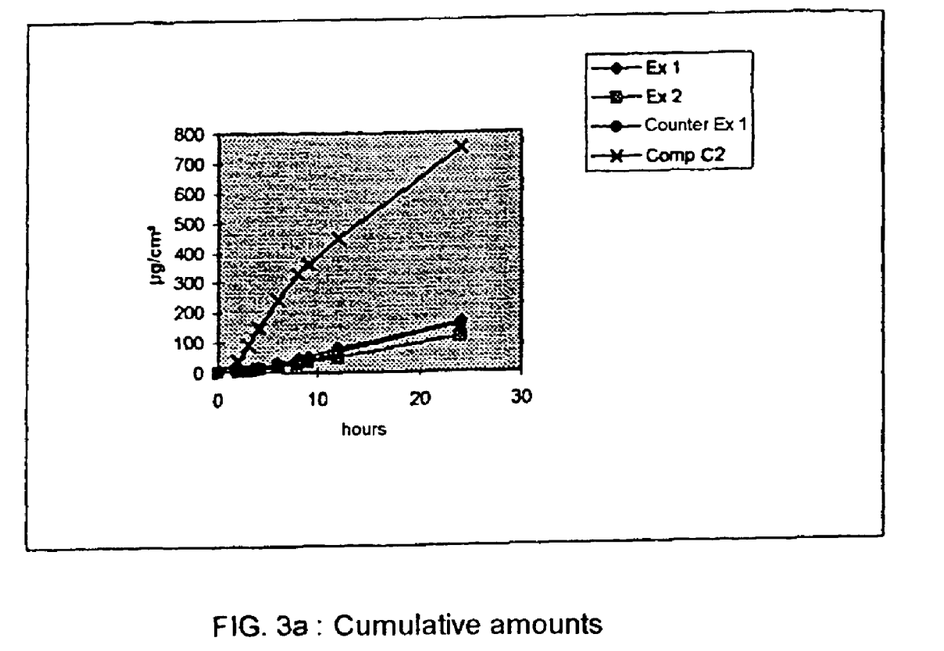
FIGS. 3a and 3b represent the amounts of testosterone released ex vivo onto animal skin, either as a cumulative amount ($\mu g/cm^2$) or as a flow ($\mu g/cm^2$/hour) in the case of the various formulations of examples 1 and 2 according to the invention and of the counterexample 1, and in the case of a transdermal device previously known and marketed under the brand name Androderm® by the company Theratech (comparative device C3).
Figure 3B:
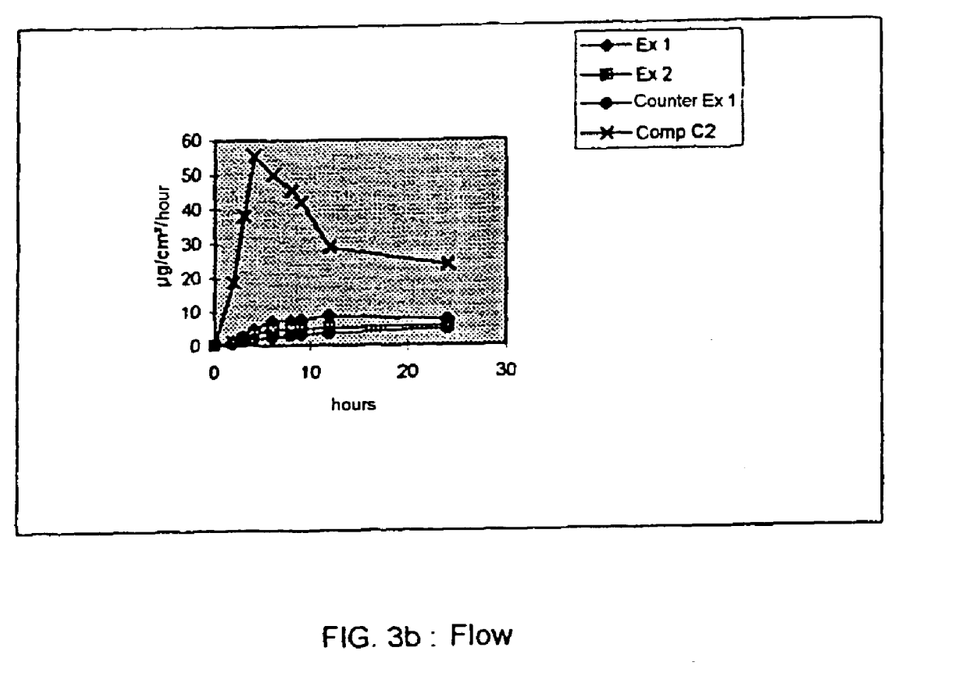
Figure 4A:
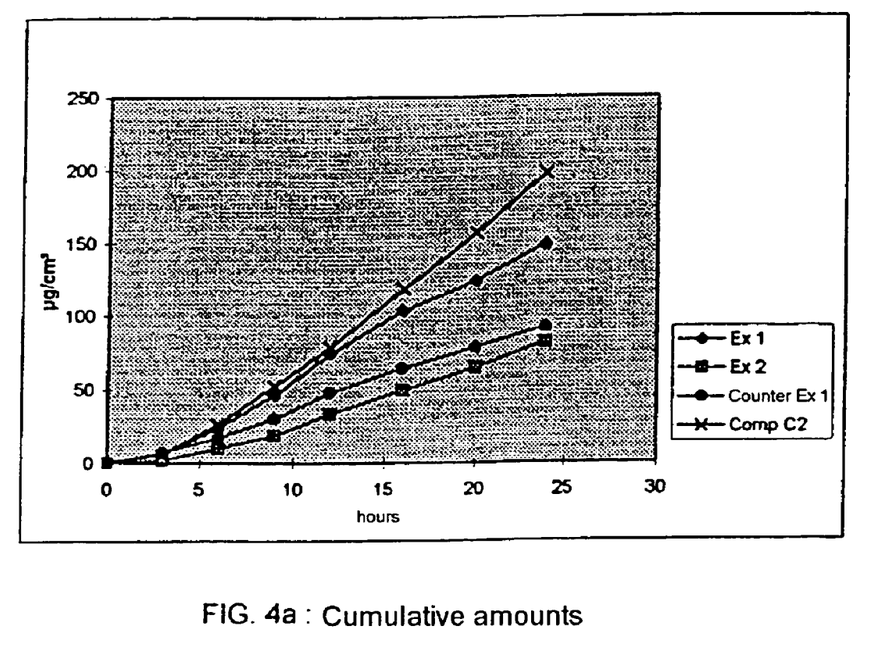
FIGS. 4a to 4d represent the amounts of testosterone released ex vivo onto human skin either as a cumulative amount ($\mu g/cm^2$) or as a flow ($\mu g/cm^2$/hour) in the case of the formulations of examples 1 and 2 according to the invention and of the counterexample 1, and in the case of a transdermal device previously known and marketed under the brand name Androderm® by the company Theratech (comparative device C2).
Figure 4B:
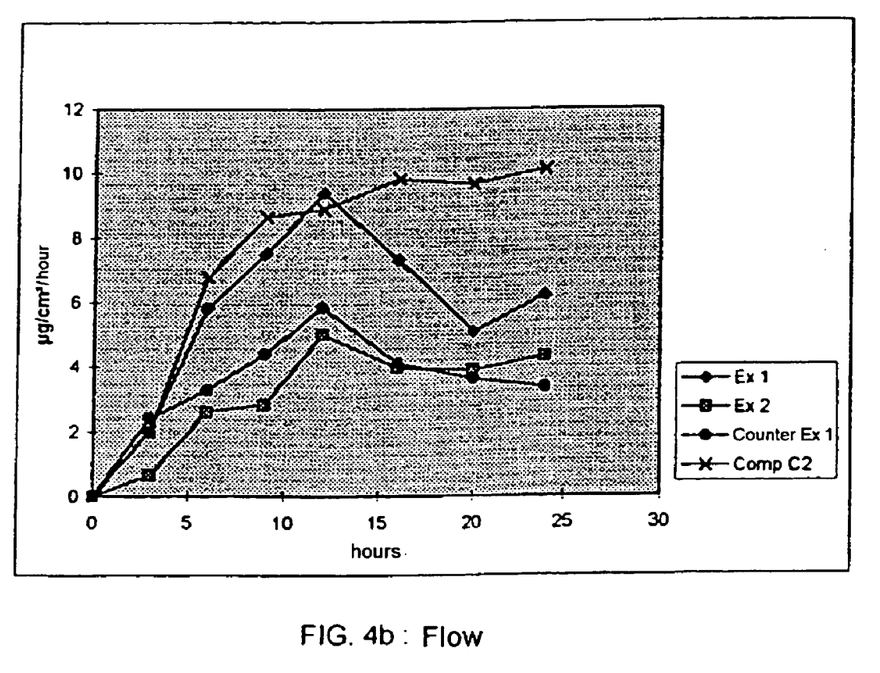
Figure 4C:
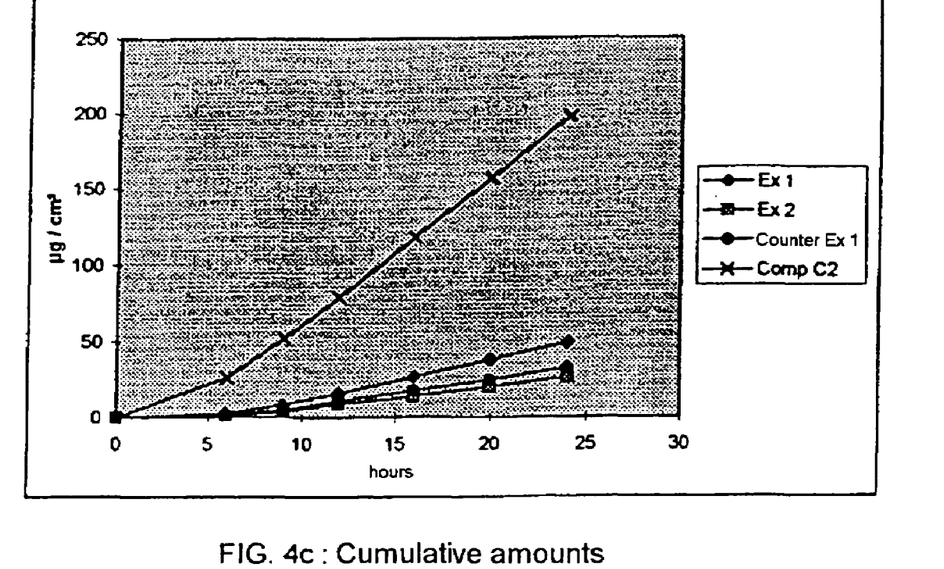
Figure 4D:
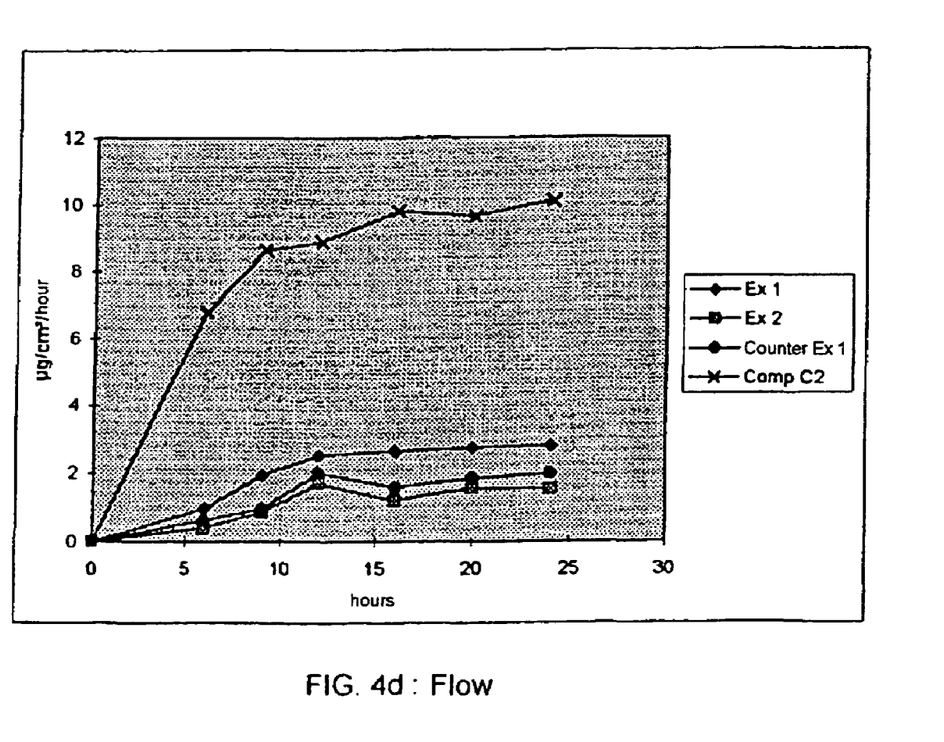
Figure 5:
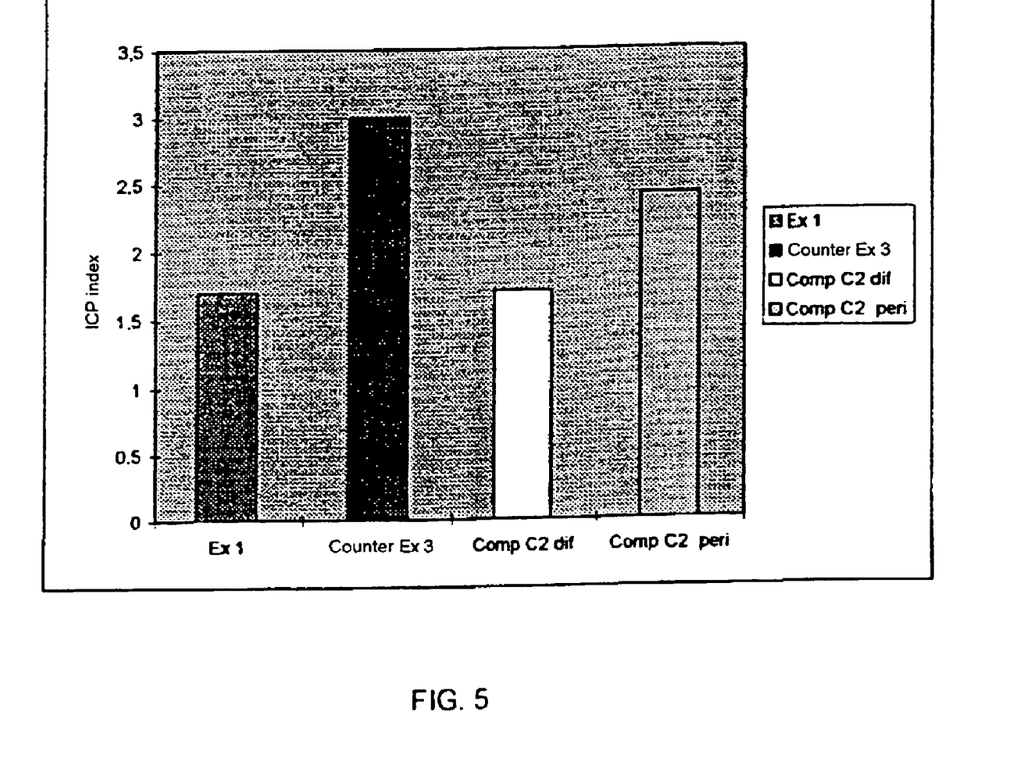
FIG. 5 represents the primary skin irritation indices for comparing as a first measure the tolerance of different formulations.
Figure 6:
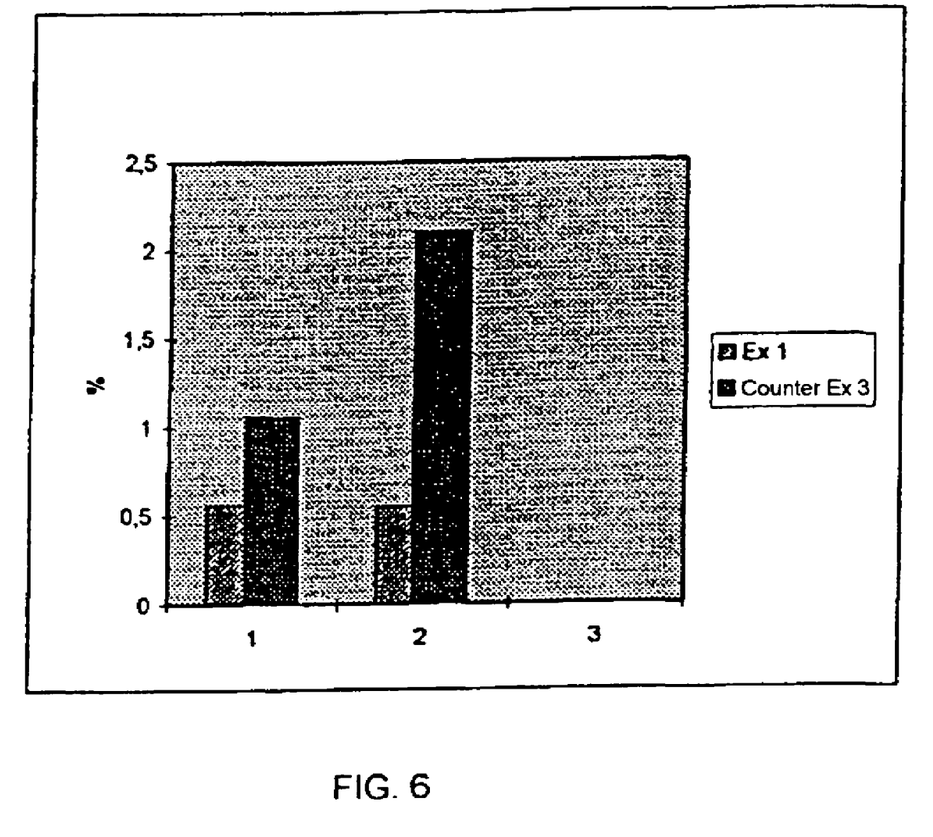
FIG. 6 represents the amounts of degradation products detected in two compositions which differ by the presence or absence of the polyvinylpyrrolidone formulation adjuvant.
Figure 7:
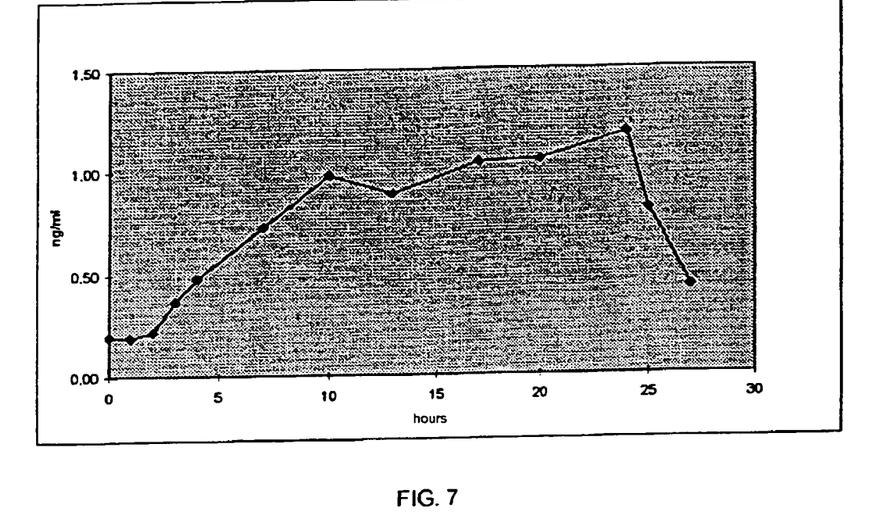
FIG. 7 represents the average levels of testosterone in the plasma obtained from 5 menopausal women after administration for 24 hours of a patch according to the invention.
Figure 8:
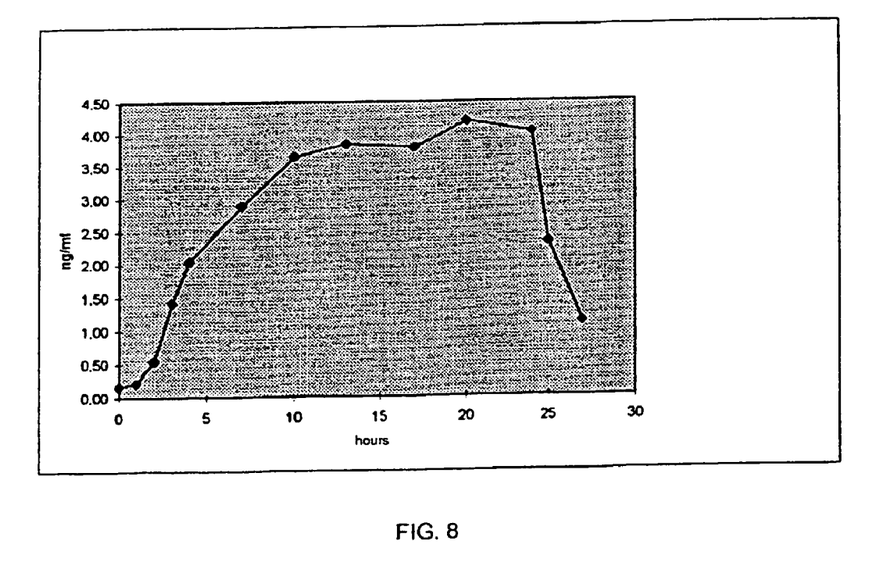
FIG. 8 represents the average levels of testosterone in the plasma obtained from 5 menopausal women after administration for 24 hours of two patches according to the invention.

This appears to result mainly from the specific characteristics of the adhesive matrix formulation per se:

a) the problems of testosterone solubility in the adhesive have been solved by means of selecting constituents that are more particularly suitable for dissolving large amounts of active principle. It has been found to be very judicious to use the solvent power of specific organic compounds such as DEET. In particular, it has been possible to incorporate into a matrix patch an amount of testosterone per $cm^2$ that is substantially equal to that present in reservoir patches, such as the Androderm® reservoir patch sold by the company Theratech (comparative device C2) that are generally better suited to this constraint:

b) as with all matrix transdermal devices, the device according to the invention comprises a skin-patch interface largely saturated with active principle, responsible for the transcutaneous passage via the phenomenon of passive diffusion. Nevertheless, given the high solubility of testosterone in solvent DEET, it was necessary to control the manufacturing process fully, and in particular the drying step, in order to ensure an advantageous state of supersaturation. Now, although such a supersaturation is conventionally encountered in the formulation of transdermal devices, it leads in many cases to an unstable physicochemical state of the active principle, characterized by the occurrence of crystallization phenomena of said active principle. The selection of formulation adjuvants, in particular of polyvinylpyrrolidone, has considerably improved the physicochemical stability of the patch without, however, placing the pharmacotechnical characteristics of said patch in doubt;

c) an important aspect of the invention is that this addition of polyvinylpyrrolidone leads to an improvement in the tolerance of the finished product, which is an advantage in terms of adherence of the patient to the treatment, and of efficacy (see FIG. 5);

d) another important aspect of the invention is that this addition of polyvinylpyrrolidone leads to improved physicochemical stability of the active principle in the adhesive matrix layer. Thus, this matrix layer, whose acid nature is, in principle, unfavorable to the stability of testosterone, is capable, surprisingly, of preserving the degradation of the testosterone, under conditions of stability (see FIG. 6);

e) a particularly advantageous aspect of the invention is the simultaneous presence of DEET and of PVP;

f) finally, it should be noted that the spectacular performance qualities of the matrix device according to the invention are obtained without the need to use permeation promoters per se for the testosterone, which, as already mentioned above, are generally more or less well tolerated and which, given the particular conditions of an occlusive administration, may be responsible for skin intolerance phenomena. Thus, the device according to the invention may advantageously be free of permeation promoter(s) per se. In addition, the non-necessity for permeation promoters is also a considerable advantage since these compounds are, in the majority of cases, liable to plasticize the adhesives into which they are incorporated and thus considerably modify their intrinsic properties. In these cases, a person skilled in the art must employ corrective agents of tackifying type, which are therefore not needed either for the preparation of device according to the invention, resulting in an advantageous saving in time and money.

The transdermal devices according to the invention are prepared according to the techniques generally used by those skilled in the art; these techniques are those of mixing, coating, drying, laminating, splitting and cutting.

A subject of the present invention is also a process for preparing the transdermal device as described above.

The process according to the invention is characterized in that it comprises the steps consisting:

a) in preparing, in a mixer, with stirring, a solution of testosterone or a derivative thereof in a first manufacturing solvent, preferably in tetrahydrofuran (THF);

b) in incorporating, into the solution thus obtained, a second manufacturing solvent, preferably chosen from ethanol and isopropanol or a mixture thereof, and also the solvent for testosterone or its derivative, which is intended to be present in the device, preferably N,N-diethyl-m-toluamide (DEET);

c) in gradually incorporating, with stirring, in a separate mixer of homogenizer, the formulation adjuvant for the matrix layer, preferably polyvinylpyrrolidone, into the self-adhesive polymer; and then d) in incorporating the mixture obtained at the end of step b) into that obtained in step c) so as to obtain a final homogeneous mixture; and e) in coating the homogeneous mixture thus obtained, at a temperature of between 50° C. and 110° C., onto a final support of polyester type or an antiadhesive temporary intermediate support, at a rate of from 50 to 150 $g/m^2$, this weight per unit area being measured on the dry film;

f) in drying the coating thus obtained, by gradual drying at a temperature of between 50° C. and 110° C., so as to evaporate the manufacturing solvents (for example THF and alcohol) and, where appropriate, to allow the crosslinking of the adhesive polymer.

Variants to the process as described above are recommended and characterized by:

preparing a separate premix containing the PVP and ethanol;

omitting the THF and replacing it with ethanol;

using a drying operation of short infrared type.

Advantageously, the high solubility of testosterone in tetrahydrofuran and also the compatibility of this highly polar solvent with the main components of the formulation have been demonstrated.

Given this high solubility of testosterone in THF, which is of the order of 27% m/m, the dissolution with stirring in step a) presents no particular difficulty. Moreover, in the context of the present invention, a solution of testosterone in THF will preferably be used in order to facilitate the mixing of the active principle in the adhesive acrylic copolymer.

Step c) should lead to the preparation of a homogeneous mixture freed of all lumps, which constitutes one of the characteristics of this process. Said process may be performed at room temperature, which presents an advantage over other techniques, for example "hot melt" techniques which generally place the active principle under greater stress.

At the end of coating, the dried film is laminated onto a support film. Depending on the case, the film obtained in the above step is then transferred onto the final support selected. The coating obtained should generally undergo steps of splitting and then final cutting of the devices before packaging according to one or other of the possible systems, a sachet or a blister pack.

Finally, a [lacuna] of the present invention is also the transdermal device as described above, for its use as a therapeutically active product in a medicinal product.

One subject of the invention is, in particular, the use of the transdermal device as defined above, for preparing a medicinal product intended for a testosterone replacement therapy.

Such a medicinal product is intended for a daily, weekly or twice-weekly testosterone replacement therapy.

More particularly, a subject of the invention is the use of the transdermal device as defined above, as a medicinal product intended for treating and/or preventing hypogonadism, for treating and/or preventing andropause disorders, for treating and/or preventing sexual impotence, for treating and/or preventing fertility disorders in men, for treating and/or preventing oligospermy and, finally, for treating and/or preventing premature ejaculation.

In the text hereinbelow, the examples are intended to illustrate the present invention and in particular should not in any way be interpreted as possibly limiting its scope.

Moreover, the figures attached hereto are explained below.

EXAMPLE 1

Preparation of a Patch According to the Invention 72 g of testosterone and 271 g of tetrahydrofuran are introduced into a mixer and the mixture is stirred at room temperature for at least 15 minutes. Next an aliquot portion of the solution obtained is isolated, i.e. a sample of 70 g to which are added 45 g of ethanol and 38 g of DEET. This premix is stored until its next use.

413 g of acrylic copolymer sold by the company National Starch & Company under the name Duro-Tak 387–2052® are introduced into a homogenizer-mixer which is also a transfer container. Next, polyvinylpyrrolidone, sold under the name Kollidon K30 by the company BASF, is gradually added portionwise with continued stirring and under vacuum. The polyvinypyrrolidone is not readily soluble in the solvent medium of the acrylic copolymer and, at this stage in the manufacture, it is found that the addition of the initial premix significantly improves the ability of the polyvinylpyrrolidone to be homogeneously dispersed in the adhesive.

Stirring is continued until a homogeneous mixture is obtained and, if necessary, the mixture is then degassed for about 30 minutes.

This final mixture is transferred into the feed hopper of a coating head which allows an amount of about 120±10 $g/m^2$ to be applied to a silicone polyester support. The support is dried by applying a temperature gradient of between 50° C. and 100° C. in order to evaporate off the manufacturing solvents and to allow the acrylic adhesive to crosslink. As a general rule, it is desirable to control this step fully, which contributes largely towards the quality of the finished product; according to said invention, this temperature gradient is associated with the possibility of varying the method of drying, by preferentially applying, in a first stage, a "strong jet of hot air" method and then, in a second stage, a "short infrared" method. At the end of drying, the adhesive matrix in dry form is laminated onto a polyester support film. The rolls thus obtained are then split into intermediate products of smaller width, which are themselves then cut to the desired size of the finished product. These finished products are then packaged either in sachets or in blister packs.

EXAMPLE 2

Preparation of a Patch According to the Invention

The process is performed in a similar manner to example 1, replacing the acrylic copolymer Duro-Tak 387–2052 with a self-crosslinking acrylic copolymer, in the form of a solution containing about 28% w/v of butyl acrylate, 2-ethylhexyl acrylate, acrylic acid, 2-hydroxyethyl acrylate, methyl methacrylate and, as crosslinking agent, aluminum acetylacetonate and t-amyl peroxypivalate, said "ready-to-use" adhesive copolymer having a glass transition temperature of −26° C. and being sold by the company National Starch & Chemical under the name Duro-Tak 87-2074®.

EXAMPLE 3

Preparation of a Patch According to the Invention

The process is performed in a similar manner to example 1, reducing the amount of the solvent for the active principle, i.e. an amount of N,N-diethyl-m-toluamide in the mixture before coating, of the order of 6%.

EXAMPLE 4

Preparation of a Patch According to the Invention

The process is performed in a manner similar to that of example 1, replacing the polyvinylpyrrolidone with another polymer, preferably sodium carboxymethyl-cellulose, sold under the name Carmellose® sodium by the company Aqualon.

EXAMPLE 5

Preparation of a Patch According to the Invention

The process is performed in a manner similar to that of example 1, replacing the polyvinylpyrrolidone with another polymer, preferably a xanthan gum, sold under the name Keltrol CR® by the company Kelco.

EXAMPLE 6

Preparation of a Patch According to the Invention

The process is performed in a manner similar to that of example 1, replacing the acrylic copolymer Duro-Tak 387-2052 with a non-self-crosslinking acrylic copolymer, in the form of a solution containing about 28% w/v of butyl acrylate, 2-ethylhexyl acrylate, acrylic acid, 2-hydroxyethyl acrylate, methyl methacrylate, said "ready-to-use" adhesive copolymer having a glass transition temperature of −26° C. and being sold by the company National Starch & Chemical under the name Duro-Tak 87-2051®.

COUNTEREXAMPLE 1

The process is performed in a manner similar to that of example 2, adding to the active premix a permeation promoter in the form of 3% of sorbitan laurate (CAS No. 1338-39-2) sold by the company SEPPIC under the name Montane 20®.

COUNTEREXAMPLE 2

The process is performed in a manner similar to that of example 2, adding to the active premix a permeation promoter in the form of 3% soybean phospholipids sold by the company Lucas Meyer under the name Pro-Lipo 242B®, or by the company Nattermann under the name Phosal 50PG®.

COUNTEREXAMPLE 3

The process is performed in a manner similar to that of example 1, but the composition described does not contain any additional polymer derivative other than the adhesive.

COMPARATIVE DEVICE C1

This is the product sold by the company Alza under the brand name Testoderm CIII®. This matrix transdermal device for scrotal application is free of promoters and, consequently, is more particularly suitable for performing in vitro protocols intended to select the best permeation promoters of this active principle.

COMPARATIVE DEVICE C2

This is the device sold under the brand name Androderm 5 MG/DAY® by the company Theratech or of the version delivering only 2.5 mg/day. This reservoir device consists of an aqueous-alcoholic testosterone gel based on hydroxypropylcellulose, containing permeation promoters such as methyl laurate and glyceryl monooleate. The diffusing surface, consisting of a control membrane, is centered around a peripheral adhesive portion which allows the patch to be held on a nonscrotal application region.

COMPARATIVE DEVICE C3

This is the comparative device C2 but limited to the aqueous-alcoholic gel part containing the active principle, that is to say freed of the flow-control membrane and of the adhesive crown.

Several tests were necessary in the course of the development of the transdermal device according to the invention.

Studies for selecting the components of the adhesive matrix other than the actual adhesive are useful and involve solubility and in vitro permeation tests. To evaluate the solubilizing power of different components, solubility studies at saturation are performed.

The analysis in table I below makes it possible to identify several categories of products, namely:
  products capable of dissolving large amounts of testosterone (>20% m/m) which are also common cosolvents for adhesive acrylic polymers, for instance ethanol and THF;
  other products capable of dissolving amounts of between 4 and 15% m/m of testosterone and which are permeation promoters cited for certain active principles including sorbitan esters or N,N-diethyl-m-toluamide;
  less advantageous products, for which the solubility of the active principle does not exceed 4% m/m.

TABLE I

| Solubility at saturation of testosterone in: | |
|---|---|
| | % m/m |
| Cyclohexane | 0.06 |
| Methyl laurate | 1.43 |
| Polysorbate 80 | 2.62 |
| Sorbitan laurate | 4.12 |
| Ethyl acetate | 4.45 |
| Lysophosphatidylcholine | 6.96 |
| Isopropanol | 12.80 |
| N,N-Diethyl-m-toluamide | 13.95 |
| Laurylpyrrolidone | 15.90 |
| Ethanol | 22.12 |
| Tetrahydrofuran | 27.01 |

As regards the second category of products, it is more particularly advantageous to check their permeation-promoting effect with respect to the active principle according to the invention. Ex vivo studies of permeation on animal skin are carried out using a reference product whose kinetics constitute a "blank", and then after initial pretreatment of the skin with the promoter compound. The ratio of the cumulative amount at 24 hours of the test relative to the "blank" gives the permeation index "PI" factor or "enhancement factor". A permeation index of close to 1 means that the test product has no promoting effect for the active principle under consideration and under the operating conditions used. A classification is then possible according to the indications of table II below.

TABLE II

| Permeation index | |
|---|---|
| 2-Octyldodecanol | 0.86 |
| DEET | 0.95 |
| Methyl laurate | 1.24 |
| Propylene glycol myristate | 2.81 |
| Glyceryl monooleate | 8.79 |
| Lysophosphatidylchloline | 9.18 |
| Laurylpyrrolidone | 11.27 |
| Sorbitan laurate | 11.70 |

Analysis of the data given in tables I and II allows the selection of the components of the adhesive matrix layer and more specifically that of the compounds that are both solvents for the testosterone and cosolvents for the adhesive acrylic polymer in combination with other solvents, for instance N,N-diethyl-m-toluamide, which lacks any testosterone-promoting effect. This step thus made it possible to incorporate into a transdermal device of matrix type an amount of active principle close to that contained in the Androderm® patch reservoir comparative device C2, and greater than 0.5 mg/cm$^2$.

The yields of the devices according to the invention are generally determined from measurements of the amounts of hormones released in 24 hours on a model of skin ex vivo, either of animal origin or of human origin. In the first case, it involves quantifying the amount of testosterone released by a transdermal device with a surface area of 4.4 cm$^2$, placed on the surface of a sample of "nude" male mouse abdominal skin, in a static cell of "Franz" cell type, the receiving compartment of which contains 22 ml of a water (0.9% NaCl)-ethanol (75/25) receiving phase maintained at 32° C. Samples are taken from the receiving compartment at 2, 3, 4, 6, 8, 9, 12 and 24 hours and an aliquot is then assayed by liquid chromatography. The tests are performed for a same test on 5 samples of skin and the results given in table III reflect the average amounts released expressed in the form of a flow (μg) per unit of surface area (cm$^2$) and per unit of time (hour):

TABLE III

| | Flow comparison (μg/cm$^2$/hour) | | | | | | | | |
|---|---|---|---|---|---|---|---|---|---|
| | 0 | 2 h | 3 h | 4 h | 6 h | 8 h | 9 h | 12 h | 24 h |
| Ex 1 | 0 | 1.4 | 2.73 | 4.90 | 7.07 | 7.2 | 7.41 | 8.73 | 7.49 |
| Ex 2 | 0 | 1.0 | 2.02 | 3.40 | 4.69 | 4.62 | 4.62 | 5.2 | 6.01 |
| Counter Ex 1 | 0 | 0.5 | 0.97 | 1.61 | 2.35 | 2.75 | 3.19 | 3.65 | 5.03 |
| Comp C2 | 0 | 18.6 | 38 | 55.45 | 50.0 | 45.48 | 42.10 | 28.96 | 23.64 |

These tests make it possible both to differentiate the release characteristics of various formulations of matrix type and to visualize the differences in kinetics with respect to another device of reservoir type. As a general rule, it is preferable to perform the same type of tests using human skin obtained from surgical biopsies. Specifically, the differences in inter-species skin permeability are known as not making it possible to predict with sufficient reliability the amounts which will be released in vivo from a single permeation test performed on animal skin. In this case, it involves quantifying the amount of testosterone released by a transdermal device with a surface area of 5 cm$^2$, applied to a sample of human skin with a surface area of 2.02 cm$^2$ obtained from cosmetic surgery, stored at −20° C., thawed at +4° C. and then dermatomed at 350 μm, in a static cell of "Franz" cell type, the receiving compartment of which contains 4 ml of an ultrapure water-ethanol (75/25) receiving phase maintained at 37° C. Samples are taken from the receiving compartment at 3, 6, 9, 12, 16, 20 and 24 hours and an aliquot is then assayed by liquid chromatography. The tests are performed for the same test on 5 samples of skin and 2 different donors; the results given in table IV reflect the average values obtained with regard to the amounts released expressed in the form of cumulative amounts for donor No. 1:

TABLE IV

| | Comparative cumulative amounts μg/cm$^2$ | | | | | | | |
|---|---|---|---|---|---|---|---|---|
| | 0 | 3 h | 6 h | 9 h | 12 h | 16 h | 20 h | 24 h |
| Ex 1 | 0 | 5.99 | 23.49 | 46.05 | 74.2 | 103.47 | 123.78 | 148.68 |
| Ex 2 | 0 | 1.96 | 9.75 | 18.22 | 33.24 | 49.07 | 64.56 | 81.83 |
| Ex 3 | 0 | 7.19 | 16.96 | 30.09 | 47.64 | 64 | 78.46 | 91.85 |
| Comp C2 | 0 | 6.0 | 26.32 | 52.23 | 78.88 | 118.14 | 156.77 | 197.29 |

The results of table IV show that one of the formulations (example 1) according to the invention allows the release of amounts of testosterone at 24 hours that are greater than those released by the comparative device C2. Said comparative device is characterized by a surface area for active release of 15 cm$^2$, of which the product by the cumulative amount per cm$^2$ at 24 hours allows the amount which would theoretically be released in vivo to be calculated, i.e. 2.95 mg/24 hours. As regards the matrix device according to the invention, and more particularly the device described in example 1, the same product of the cumulative amount per cm$^2$ at 24 hours by a theoretical surface area of 40 cm$^2$ allows the amount which would theoretically be released in vivo to be calculated, i.e. 5.94 mg/24 hours. Given the actual surface areas of the devices (40 cm$^2$ for the formulations of examples 1 to 3, and 15 cm$^2$ for the comparative device C2), it is observed that larger amounts are released for the formulations of the present invention.

Finally, tests intended to characterize the in vitro release of testosterone from these devices were performed on the matrix devices according to the invention. These tests generally adapted from the recommendations of various pharmacopeias, including the US Pharmacopeia, are called dissolution tests. Each reactor of which the "rotating pallet" dissolution machine is composed is equipped with a watch glass onto which is placed the test device using a double-sided adhesive tape. A dissolution medium composed of water/ethanol mixture (90/10) is introduced into each reactor, heated to 37° C. and stirred at 50 rpm. Samples are taken, more particularly at times 30 min, 1, 4, and 8 hours, on which assays are performed by liquid chromatography. Table V below shows the average values obtained from 6 tests performed on the same sample.

TABLE V

Comparative in vitro dissolution %

|  | 0 | 0.5 h | 1 h | 4 h | 8 h |
|---|---|---|---|---|---|
| Ex 1 | 0 | 23.30 | 36.30 | 73.90 | 91.10 |
| Ex 2 | 0 | 16.30 | 26.90 | 57.50 | 76.30 |
| Counter Ex 1 | 0 | 16.50 | 27.60 | 58.90 | 77.80 |

This test essentially makes it possible to characterize the in vitro release with concern for routine monitoring of the matrix device. It is more particularly relevant to reveal identical trends between the dissolution profiles obtained in vitro and the permeation kinetics obtained ex vivo and presented in tables III and IV.

Finally, it is again found that the matrix transdermal devices according to the invention are remarkably well tolerated, according to the primary skin irritation tests, the results of which are given in table VI below, and which were carried out under the terms of the Journal Officiel de la Republique Francaise 1982.

TABLE VI

|  | Primary skin irritation index | Classification |
|---|---|---|
| Ex 1 | 1.7 | slightly irritant |
| Ex 2 | 2.0 | slightly irritant |
| Counterexample 1 | 1.6 | slightly irritant |
| Counterexample 3 | 3.0 | irritant |
| Comp C2 diffusing part | 1.71 | slightly irritant |
| Comp C2 adhesive part | 2.42 | irritant |

It is advantageously found that the devices according to the invention are at least as well tolerated as the product Androderm®. For the latter product, it is found that the adhesive periphery not containing any active principle is less well tolerated than the central diffusing surface. It is also found that the presence of the polyvinylpyrrolidone formulation adjuvant allows better skin tolerance of the composition as described in example 1.

The invention claimed is:

1. A self-adhesive transdermal device for administering testosterone and/or at least one derivative thereof, which comprises, successively, at least, one support layer, one self-adhesive matrix layer and one detachable protective layer, said adhesive matrix layer comprising, relative to the total weight of the matrix layer:
   a) 40% to 80% by weight of at least one self-adhesive polymer selected from acrylic polymers, with an acid number of between 10 and 70, with an acid functionality and a glass transition temperature of between −70° C. and −20° C.;
   b) 5% to 25% by weight of at least one formulation adjuvant for the matrix layer selected from polymers with a number-average molecular mass of between 2 500 and 3 000 000;
   c) 5% to 20% by weight of at least one solvent selected from the group consisting of solvents for testosterone and derivatives thereof, in which the solubility of the testosterone or derivative thereof is between 5% and 20% m/m;
   d) 2% to 10% by weight of testosterone and/or at least one derivative thereof, as a supersaturated solution, and wherein the matrix layer does not comprise a permeation promoter of testosterone.

2. The device of claim 1, wherein the self-adhesive polymer is a polymer of a (meth)acrylic acid monomer and of at least one monomer selected from the group consisting of C1–C6 alkyl (meth)acrylate, 2-(C1–C6 alkyl)hexyl (meth)acrylate, vinyl acetate, glycidyl (meth)acrylate and 2-hydroxy (C1–C6 alkyl) (meth)acrylate monomers.

3. The device of claim 2, wherein the self-adhesive polymer is a polymer of a (meth)acrylic acid monomer and of at least one monomer selected from the group consisting of methyl (meth)acrylate, butyl (meth)acrylate, 2-ethylhexyl (meth)acrylate, vinyl acetate, glycidyl (meth)acrylate and 2-hydroxyethyl (meth)acrylate monomers.

4. The device of claim 1, wherein the matrix layer is crosslinked.

5. The device of claim 1, wherein the self-adhesive polymer is crosslinked.

6. The device of claim 1, wherein the matrix layer is not crosslinked.

7. The device of claim 1, wherein self-adhesive polymer is not crosslinked.

8. The device of claim 1, wherein the formulation adjuvant is selected from the group consisting of polymers of 1-vinyl-2-pyrrolidone monomer, polysaccharides and cellulose derivatives, and mixtures thereof.

9. The device of claim 8, wherein the formulation adjuvant is selected from the group consisting of polyvinylpyrrolidone, xanthan gums and sodium carboxymethylcellulose, and mixtures thereof.

10. The device of claim 1, wherein the solvent is a solvent for testosterone and/or its esters, selected from the group consisting of N,N-diethyl-m-toluamide, 2-octyldodecanol, crotamiton and propylene glycol dipelargonate, and mixtures thereof.

11. The device of claim 1, wherein the self-adhesive polymer is a polymer selected from acrylic acid, 2-ethylhexyl acrylate, vinyl acetate and butyl acrylate monomers, this polymer being crosslinked and having an acid number of between 10 and 70 and also a glass transition temperature of between −100° C. and −10° C., the formulation adjuvant is polyvinylpyrrolidone with a number-average molecular mass of between 44 000 and 54 000, and the solvent is N,N-diethyl-m-toluamide.

12. The device of claim 1, wherein the matrix layer comprises, relative to its total weight:
   a) 63% to 73% by weight of at least one self-adhesive polymer selected from acrylic acid, 2-ethylhexyl acrylate, vinyl acetate and butyl acrylate monomers, this polymer being crosslinked and having an acid number of between 10 and 70 and also a glass transition temperature of between −100° C. and −10° C.;
   b) 5% to 25% by weight of polyvinylpyrrolidone with a number-average molecular mass of between 44 000 and 54 000;
   c) 9% to 15% by weight of N,N-diethyl-m-toluamide;
   d) 4% to 6% by weight of testosterone.

13. The device of claim 1, wherein the matrix layer also comprises at least one antioxidant selected from butylhydroxytoluene (BHT), butylhydroxyanisole (BHA), ascorbyl palmitate, α-tocopherol and its esters, citric acid and propyl gallate, and mixtures thereof.

14. The device of claim 13, wherein the antioxidant is present in the matrix layer, relative to the total weight of the matrix layer, in a proportion of between 0.1% and 2% by weight.

15. A process for preparing the transdermal device of claim 1, which comprises the steps of:
- a) preparing, in a mixer, with stirring, a solution of testosterone or a derivative thereof in a first manufacturing solvent;
- b) incorporating, into the solution thus obtained, a second manufacturing solvent and also the solvent for testosterone or its derivative, which is intended to be present in the device;
- c) gradually incorporating, with stirring, in a separate mixer or homogenizer, the formulation adjuvant for the matrix layer into the self-adhesive polymer; and then
- d) incorporating the mixture obtained at the end of step b) into that obtained in step c) so as to obtain a final homogeneous mixture; and
- e) coating the homogeneous mixture thus obtained, at a temperature of between 50° C. and 110° C., onto a final polyester support or an antiadhesive temporary intermediate support, at a rate of from 50 to 150 g/m$^2$, this weight per unit area being measured on the dry film;
- f) drying the coating thus obtained, by gradual drying at a temperature of between 50° C. and 110° C., so as to evaporate the manufacturing solvents and, where appropriate, to allow the crosslinking of the adhesive polymer.

16. The process of claim 15, wherein the solvent for testosterone or its derivative is N,N-diethyl-m-toluamide (DEET).

17. The process of claim 15, wherein the formulation adjuvant for the matrix layer is polyvinylpyrrolidone (PVP).

18. The device of claim 1, which is a medicinal product which is therapeutically effective for testosterone replacement therapy.

19. A method of treating a living animal body in need of testosterone replacement therapy comprising the use of the device of claim 1 for administering a medicinal product which is effective for such therapy.

20. The method of claim 18, wherein the medicinal product is administered in a daily, weekly or twice-weekly testosterone replacement therapy.

21. The method of claim 18, wherein the medicinal product is administered for treating hypogonadism.

22. The method of claim 18, wherein the medicinal product is administered for treating andropause disorders.

23. The method of claim 19, wherein the medicinal product is administered for treating sexual impotence.

24. The method of claim 19, wherein the medicinal product is administered for treating fertility disorders in men.

25. The method of claim 19, wherein the medicinal product is administered for treating oligospermy.

26. The method of claim 19, wherein the medicinal product is administered for treating premature ejaculation.

* * * * *

UNITED STATES PATENT AND TRADEMARK OFFICE
CERTIFICATE OF CORRECTION

| | |
|---|---|
| PATENT NO. | : 7,018,648 B2 |
| APPLICATION NO. | : 09/979757 |
| DATED | : March 28, 2006 |
| INVENTOR(S) | : Michel Sournac et al. |

It is certified that error appears in the above-identified patent and that said Letters Patent is hereby corrected as shown below:

On the title Page Filing Date: "Nov. 26, 2001" should be -- Nov. 19, 2001 --.

Column 16, Line 13: " claim 18, " should be -- claim 19, --.

Column 16, Line 16: " claim 18, " should be -- claim 19, --.

Column 16, Line 18: " claim 18, " should be -- claim 19, --.

Signed and Sealed this

Twenty-second Day of August, 2006

JON W. DUDAS
*Director of the United States Patent and Trademark Office*